United States Patent [19]

Wright

[11] Patent Number: 5,354,658
[45] Date of Patent: Oct. 11, 1994

[54] NON-RADIOACTIVE METHOD FOR DETECTING A LABELLED SEGMENT AND A SOLUTION OR COMPOSITION THEREFOR

[76] Inventor: Dennis Wright, 2925 E. Wisconsin Apt. D., Great Lakes, Ill. 60088

[21] Appl. No.: 10,344

[22] Filed: Jan. 28, 1993

[51] Int. Cl.$^5$ .................... C12Q 1/68; G01N 33/53
[52] U.S. Cl. ........................ 435/6; 435/7.1; 435/7.94; 435/21
[58] Field of Search ............ 435/6, 7.1, 7.94, 21; 935/77, 78; 530/387.1; 436/536

[56] References Cited

U.S. PATENT DOCUMENTS

| | | | |
|---|---|---|---|
| 4,215,197 | 7/1980 | Tarbutton | 435/18 |
| 4,613,569 | 9/1986 | Geisler et al. | 435/26 |
| 4,642,295 | 2/1987 | Baker | 436/87 |
| 4,645,742 | 2/1987 | Baker | 436/15 |
| 4,847,194 | 7/1989 | Quante | 435/7 |
| 4,847,196 | 7/1989 | Geisler et al. | 435/26 |
| 4,849,347 | 7/1989 | Familletti et al. | 435/26 |
| 4,956,301 | 9/1990 | Ismail et al. | 436/87 |
| 5,139,934 | 8/1992 | Stewart et al. | 435/7.92 |

OTHER PUBLICATIONS

Heegaard, Applied and Theoreti. Electropho. 1:261-2364 (1990) "Visualization of Alkaline Phosphase"....
Kugler, Histochemistry 75:99-112 (1982) "Quantitative Dehydrogenase Histochemistry".
Blake et al., Anal. Biochem 136:175-179 (1984) "A Rapid, Sensitive Method for Detection".

*Primary Examiner*—Margaret Parr
*Assistant Examiner*—Eggerton Campbell
*Attorney, Agent, or Firm*—James P. Hanrath

[57] ABSTRACT

A non-radioactive method of detecting a ligand and antiligand complex labelled with alkaline phosphatase or a tracer having alkaline phosphatase conjugated thereto comprises reacting the complex with bromo-chloro-indolyl phosphate (BCIP), phenazine methosulfate (PMS) and dimethylthiazol diphenyl tetrazolium (MTT) and allowing the reaction to proceed to produce a colored formazan or a color change indicative of the presence of the labelled complex. A solution or composition of bromo-chloro-indolyl phosphate (BCIP), phenazine methosulfate (PMS) and dimethylthiazol diphenyl tetrazolium (MTT), as well as a test kit including the same, is also provided for carrying out the chromogenic method of detection.

38 Claims, 2 Drawing Sheets

NON-RADIOACTIVE METHOD FOR DETECTING A LABELLED SEGMENT AND A SOLUTION OR COMPOSITION THEREFOR

BACKGROUND OF THE INVENTION

1. Field of the Invention

The present invention relates to a non-radioactive method and a solution or composition for the detection of a ligand and antiligand complex of a DNA or RNA nucleic acid, an antigen, a hapten, a protein, an analyte, an antibody, or an antibody complex wherein the complex is labelled with alkaline phosphatase or a tracer having alkaline phosphatase conjugated thereto, and reacted with bromo-chloro-indolyl phosphate (BCIP), phenazine methosulfate (PMS), and dimethylthiazol diphenyl tetrazolium (MTT) to produce a colored formazan or a color change indicative of the presence of the labelled complex.

2. Description of the Related Art

Labelling a segment of a DNA or RNA nucleic acid, a protein, a hapten, an antigen, an analyte, an antibody or an antibody complex such that the same can be later identified and detected is desirable in many applications, including diagnostic application of probe technologies.

Assay systems which are both rapid and sensitive have been developed to determine the concentration of a substance, for example an analyte, present in low concentration in a fluid sample. Immunoassays depend on the binding of an antigen or hapten to a specific antibody and have been particularly useful because they give high levels of specificity and sensitivity. Such assays may employ a reagent in labelled form referred to as the tracer.

For example, five basic methods of labelling nucleic acids include nick translation, primer extension, methods based on RNA polymerase, end-labelling methods, and direct labelling methods. In many probe technologies, the need for resolution and sensitivity determines the choice of label to DNA or RNA nucleic acid, proteins, or antibodies. Labels for probes are usually radioactive. Biotin is a commonly used non-radioactive label for probes which can be incorporated into polynucleotide enzymatically using biotinylated nucleotide as the substrate. Alternatively, a photoactivatable analogue of biotin upon brief irradiation with visible light may be used to form stable linkages with both single and double stranded nucleic acids. Biotin-labelled probes are detected through a variety of signal generating systems usually using avidin, a glycoprotein with an extremely high affinity for biotin, or streptavidin, an avidin-like protein. Alternatively, it has been known to label DNA with digoxigenin-labelled deoxyuridine triphosphate. After hybridization to the target DNA, the hybrids are detected by enzyme-linked immunoassay using an antibody conjugate such as biotin-conjugated with alkaline phosphatase.

Non-radioactive labels with biotin have lower sensitivity in comparison with radioactive labels. Thus, radioactive probes are used for most commercial applications of hybridization technologies requiring that probes be freshly prepared at regular intervals due to radioisotopes having short half-lives. Radioactive labels also require special safety precautions for the isotopes and proper radioactive waste disposal.

Enzymes have also often been used as labels in immunoassay. In conventional enzyme immunoassay (EIA), an enzyme is covalently conjugated with one component of a specifically binding antigen-antibody pair, and the resulting enzyme conjugate is reacted with a substrate to produce a signal which is detected and measured. The signal may be a colour change, detected with the naked eye or by a spectrophotometric technique, or may be conversion of the substrate to a product detected by fluorescence.

A convenient format for EIA is solid phase immunoassay in which one of the assay reagents is immobilized on a solid support usually in the form of a dip stick, the inside wall of a test tube or cuvette, the well of a microtiter plate, or a microporous membrane. The final step in most membrane EIA procedures is contacting a color developing reagent, such as a chromogen, with the membrane. The chromogen reacts with enzyme captured on the membrane to produce a colored product which may be detected as evidence of the presence of analyte or measured as evidence of the concentration of analyte.

Tetrazolium salts have been used for analytical purposes in the detection of reduced nicotinamideadenine dinucleotide (NADH) wherein the transference of hydrogen is catalyzed not only by enzymes, such as diaphorase, but also by 5-methylphenazinium methylsulphate (PMS) or similar substances, to thereby form deep colored formazans as a reduction indicator. Therefore, appropriate processes have been developed in this way to detect a series of substances which are important in analytical chemistry, via the NADH produced as an intermediate. Tetrazolium salts conventionally employed in dehydrogenase procedures include 3-(4.5'-dimethylthiazolyl-2)-2,4-diphenyltetrazolium bromide (MTT), 2-(p-iodophenyl)-3-(p-nitrophenyl)-5-phenyl-tetrazolium chloride (INT), 2,2',5,5'-tetra-(p-nitrophenyl)-3,3-(3-dimethoxy-4-diphenylene)-ditetrazolium chloride (TNBT), 2,2'-di-(p-nitrophenyl)-5.5'-diphenyl-3,3'-dimethoxy-4,4'-diphenylene)-ditetrazolium chloride (NBT), 2,2'-p-diphenylene-3,3',5.5'-tetraphenyl-ditetrazolium chloride (neotetrazolium chloride) (NT) and 2,3,5-triphenyltetrazolium chloride (TT).

U.S. Pat. Nos. 4,613,569 and 4,867,196 to Giesler et al. are directed to a stabilized composition of tetrazolium salts containing one to ten moles of a complex-forming acid, such as boric acid or organic hydroxypolylcarboxylic acid, which is soluble in polar solvents per mole of tetrazolium salt. The stabilizing agents are employed in previously known test systems in which the tetrazolium salts are used as indicators such as dehydrogenase procedures involving the detection of lactic acid with lactate dehydrogenase, alcohol with alcohol dehydrogenase, glycerol with glycerol dehydrogenase, glucose with glucose dehydrogenase, acetaldehyde with acetaldehyde dehydrogenase, as well as further systems which can be coupled to the above system.

The present invention provides for a non-radioactive method of detecting (as well as a solution and composition therefor) a ligand and antiligand complex labelled with alkaline phosphatase or a tracer having alkaline phosphatase conjugated thereto which comprises reacting the complex with bromo-chloro-indolyl phosphate (BCIP), phenazine methosulfate (PMS) and dimethylthiazol diphenyl tetrazolium (MTT) and allowing the reaction to proceed to reduce the dimethylthiazol diphenyl tetrazolium (MTT) and form a colored formazan or produce a color change indicative of the presence of the labelled complex.

SUMMARY OF THE INVENTION

According to the present invention there is provided a non-radioactive method of detecting a ligand and antiligand complex labelled with alkaline phosphatase or a tracer having alkaline phosphatase conjugated thereto comprising reacting said complex with bromo-chloro-indolyl phosphate (BCIP), phenazine methosfate (PMS) and dimethylthiazol diphenyl tetrazolium (MTT) and allowing the reaction to proceed to produce a colored formazan or a color change indicative of the presence of said labelled complex. The present invention also provides for a solution or composition, as well as a test kit including the same, used in the method of detection of a ligand and antiligand complex labelled with alkaline phosphatase or a tracer having alkaline phosphatase conjugated thereto in a sample to be tested that comprises a mixture of bromo-chloro-indolyl phosphate (BCIP), phenazine methosulfate (PMS) and dimethylthiazol diphenyl tetrazolium (MTT) which, when the solution added to said test sample or the composition dissolved in solution and added to the test sample, is capable of producing a colored formazan or a color change indicative of the presence of said labelled complex.

Such a method of detection has great sensitivity, namely $10^{minus\ 15}$ power, and the reaction, which can be completed in approximately twenty minutes, produces a purple formazan or a color change visible by the naked eye in from less than five minutes to approximately fifteen minutes compared to conventional BCIP-NBT detection techniques sensitive to $10^{minus\ 12}$ power which may take many hours or over a day to complete and four or more hours to visually observe. Further, the present invention requires no radioisotope labelling and its sensitivity and specificity makes it useful for hybridization techniques where radioactive labelling and autoradiography are normally required. Also, the method of detection of the present invention can be used for nucleic acid transfers for colony, plaque, in vitro, and in situ hybridizations including standard Southern, Northern, Western, and Southwestern blotting techniques provided such transfers or techniques utilize alkaline phosphatase for chromogenic detection. Further, the present invention may not require use of amplification techniques. Further, the present invention requires no stabilizing agent for the tetrazolium salt and produces an irreversible reaction. Still further, the present invention is cost and economy advantageous as it may use only one-tenth of certain chemicals in solution compared to prior art techniques.

DESCRIPTION OF THE PREFERRED EMBODIMENTS

Figure 1:
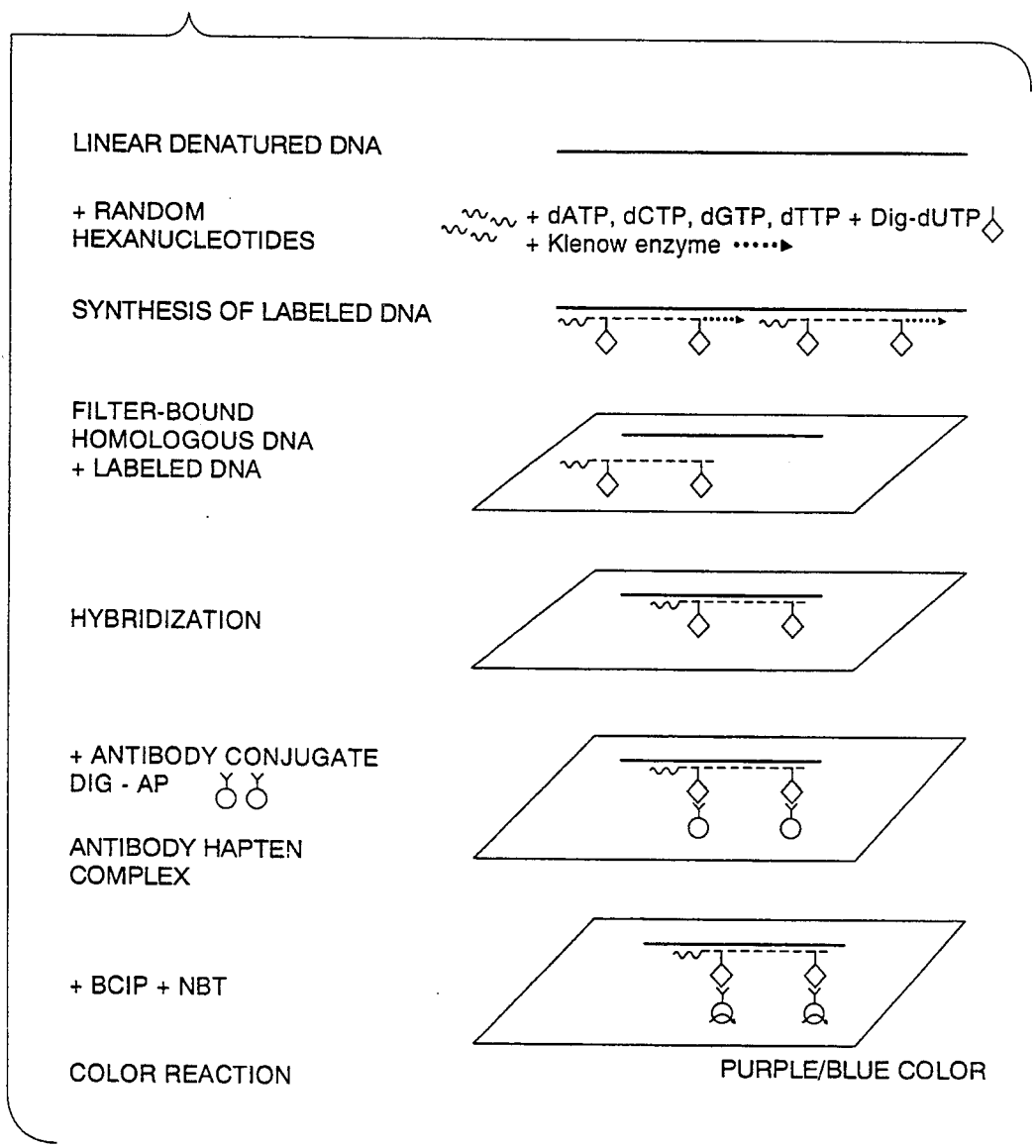
FIG. 1 illustrates a non-radioactive prior art technique for detection of a labelled and hybridized DNA segment using an antibody-conjugate of antidigoxigenin and alkaline phosphatase in an enzyme-catalyzed color reaction with bromo-chloro-indolyl phosphate (BCIP) and nitroblue tetrazolium salt (NBT).

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalence.

The present invention provides a non-radioactive method for detection of a ligand and antiligand complex of DNA or RNA nucleic acid, a hapten, an antigen, a protein, an antibody, an antibody complex, or an analyte which is labelled with alkaline phosphatase or a tracer having alkaline phosphatase conjugated thereto wherein the labelled complex is detected in a color reaction with bromo-chloro-indolyl phosphate (BCIP), phenazine methosulfate (PMS, N-methylphenazonium methosulfate, $C_{14}H_{14}N_2O_4S$, molecular weight 306.34, mp 158°-160° (dec), $\lambda max$ 386 nm, Merck Index 11,6024, FT-IR 1(2),885A), and dimethylthiazol diphenyl tetrazolium (MTT, 3-(4,5-dimethylthiazol-2-yl)-2,5-diphenyl-2H-tetrazolium bromide, $C_{18}H_{16}N_5SBr$, molecular weight 414.33, mp 195° (dec.), $\lambda max$ 378 nm, NMR 2,(2),501D, FT-IR 1(2),633 B). As used herein bromo-chloro-indolyl phosphate, also referred to as BCIP, includes 5-bromo-4-chloro 3-indolyl phosphate (BCIP, crystalline, disodium salt, $C_8H_4BrClNO_4PNa_2 \cdot H_2O$, molecular weight 370.44, mp>300°) or 5-bromo-4-chloro-2-indolyl phosphate (crystalline, disodium salt, $C_8H_4BrClNO_4PNa_2 \cdot H_2O$, molecular weight 397.5) or 5-bromo-4-chloro-3-indolyl phosphate.toluidine (powder, 4-toluidine salt, $C_8H_6NO_4BrCIP \cdot C_7H_9N$, molecular weight 433.6).

Figure 2:
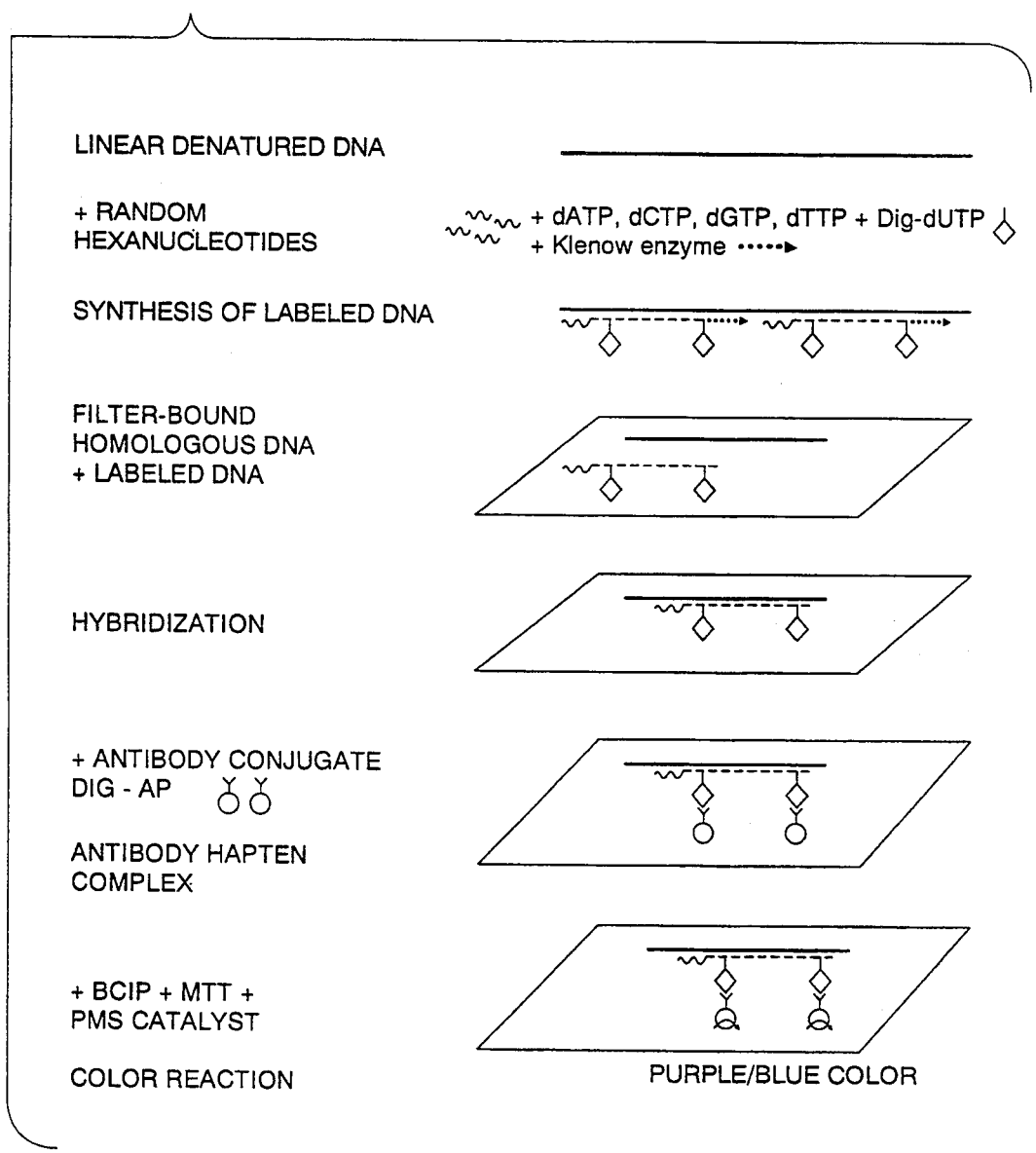
FIG. 2 illustrates the non-radioactive technique of the present invention for the detection of a labelled and hybridized DNA segment using an antibody-conjugate of antidigoxigenin and alkaline phosphatase but in a color reaction based on bromo-chloro-indolyl phosphate (BCIP) in admixture with catalyst phenazine metholsulfate (PMS) and dimethylthiazol diphenyl tetrazolium (MTT).

For example, contrary to the known non-radioactive method for detection of an antibody hapten complex illustrated in FIG. 1 of a biotin-labelled DNA using avidin and alkaline phosphatase which employs a signal generating system of nitroblue tetrazolium (NBT) in a mixture with 5-bromo 4-chloro 3-indolyl phosphate (BCIP), the present invention, as illustrated at FIG. 2, detects a antibody hapten complex of a labelled hybridized segment of DNA conjugated with alkaline phosphatase by a reaction with a mixture of 5-bromo 4-chloro 3-indolyl phosphate (BCIP), phenazine methosulfate (PMS), and dimethylthiazol diphenyl tetrazolium (MTT). When alkaline phosphatase in the system illustrated at FIG. 2 reacts with 5-bromo 4-chloro 3-indolyl phosphate (BCIP) and dimethylthiazol diphenyl tetrazolium (MTT) in the presence of a phenazine methosulfate (PMS) catalyst, the dimethylthiazol diphenyl tetrazolium (MTT) serves as a hydrogen acceptor and is converted to $MTTH_2$, a colored purple insoluble formazan complex in stoichiometric quantities which indicates a positive reaction and the presence and concentration of a labelled nucleic segment.

While immunoassay for a DNA hapten as described above and illustrated at FIG. 2 is a preferred application of the invention, one skilled in the art will immediately recognize that the method may be used in many assay procedures. For example, the chromogenic detection of present invention may be implemented in an assay wherein the ligand may be a RNA nucleic acid probe and the tracer may be a complimentary strand of RNA or DNA conjugated with alkaline phosphatase. Alternatively, the ligand may be a protein or antigen using an alkaline phosphatase label or a tracer conjugated with alkaline phosphatase. Still further, the ligand may be an analyte or an antibody or an antibody complex using an alkaline phosphatase label or a tracer conjugated with alkaline phosphatase. Assay procedures involving either direct incorporation of alkaline phosphatase to a ligand or a tracer having alkaline phosphatase conjugated thereto are well known in the art, and so long as alkaline phosphatase is present, the detection method of the present invention involving reacting the ligand-antiligand complex with bromo-chloro-indolyl phosphate (BCIP) and dimethylthiazol diphenyl tetrazolium (MTT) catalyzed by phenazine methosulfate (PMS) will provide a reliable chromogenic detection of the presence and concentration of the applicable labelled segment.

Therefore, membranes such as glass fiber, polyvinylidene difluoride, polycarbonate, nitrocellulose and nylon having a ligand bound thereto may be treated with a solution of a tracer with alkaline phosphatase. The tracer may be an antiligand having alkaline phosphatase conjugated to the ligand wherein the assay is performed by conventional sandwich or half sandwich technique. A preferred detection antigen would be alkaline phosphatase which binds to an antiligand captured on the membrane and thereby affixes the ligand to the membrane surface in direct proportion to the quantity of antiligand in the sample. Alternatively, the ligand may be conjugated by conventional methods to a binder such as biotin, avidin and streptavidin and the latter bound to the antibodies. In any event, the detection method of the present invention provides a chromogenic determination of the presence of the alkaline phosphatase segment by reacting the ligand-antiligand complex with bromo-chloro-indolyl phosphate (BCIP) and dimethylthiazol diphenyl tetrazolium (MTT) catalyzed by phenazine methosulfate (PMS) to form a purple or deep color formazan or produce a color change.

The ligand or antiligand for use with the chromogenic indication of the present invention may be from any source and each may be selected from the group consisting of an antigen, an analyte, a protein, an antibody, an antibody complex, and a hapten. Preferably, if the ligand is an antigen, then the antiligand is an antibody specific for that antigen. Likewise, if the ligand is a hapten, then the antibody preferably is an antibody specific for the hapten. If the ligand is an antibody, preferably the antiligand is an antigen specific for the antibody. If the ligand is a protein, then the antiligand is preferably an antibody specific for the protein. If the ligand is a nucleic acid, then preferably the antiligand is a complementary nucleic acid specific for that nucleic acid. If the ligand is an antibody complex, then the antiligand is preferably an antigen specific for that antibody complex.

For example, the ligand may be an endocrine hormone, such as HCG or FSH, present in body fluid, or it may be isolated from body fluid and subsequently introduced into a different liquid, such as a buffer. In other cases, the ligand may be from a source other than a body fluid, as, for example, a culture of microorganisms such as Chlamydia or a cellar extract thereof. Antibodies, such as the antibody against Lyme disease, may be assayed, or the ligand may be a hapten such as a therapeutic drug or a drug of abuse. The ligand may also be a protein such as glycoprotein 120 useful in HIV testing. Preferred ligands are antigens, most preferably viral antigens present in a body fluid, such as Adenovirus, Parainfluenza 3 virus, Herpes simplex virus (HSV), Respiratory syncytial virus (RSV), and Influenza A (Flu A).

Assay techniques involving the chromogenic indication of the present invention may also be performed by competitive assay wherein the ligand and tracer compete for antiligand binding sites. For example a ligand directly labelled with alkaline phosphatase and a tracer selected from the group consisting of an antigen, an analyte, a protein, an antibody, an antibody complex, and a hapten may compete for binding sites on the antiligand. Alternatively, the competitive assay may be a procedure wherein a ligand selected from the group consisting of an antigen, an analyte, a protein, an antibody, an antibody complex, and a hapten and a tracer having alkaline phosphatase conjugated thereto compete for binding sites on the antiligand. In the latter alkaline phosphatase tracer format, alkaline phosphatase becomes affixed to the membrane surface in inverse proportion to the quantity of ligand in the sample and the absence of colored formazan is indicative of ligand in the sample.

Labelling of ligands with alkaline phosphatase, or labelling of a tracer having alkaline phosphatase conjugated thereto to form a ligand-antiligand complex is well known in the art and deemed to be within the purview of one skilled in the art.

One may, for example, utilize the detection method of the present invention for the identification of a protein synthesized by a recombinant gene by growing cloned bacteria and transferring the same to a membrane, lysing the bacteria with chloroform, binding the first antibody with a protein, and binding a second antibody with a tracer conjugated with alkaline phosphatase such that the presence and concentration of a positive clone-first antibody protein is detected by a color reaction resultant from admixture with bromo-chloro-indolyl phosphate (BCIP), catalyst phenazine metholsulfate (PMS), and dimethylthiazol diphenyl tetrazolium (MTT).

The present invention of chromogenic detection of a ligand-antiligand complex labelled with alkaline phosphatase or a tracer having alkaline phosphatase conjugated thereto may be practiced by reacting the complex with a combined mixture containing bromo-chloro-indolyl phosphate (BCIP), phenazine methosulfate (PMS), and dimethylthiazol diphenyl tetrazolium (MTT). Such a combined mixture may further include a buffer, such as distilled water or a buffer of a mixture in solution of Tris-HCl or Tris-base, sodium chloride (NaCl), and magnesium chloride ($MgCl_2$). Preferably, the buffer has a pH of about 7 to about 11, with 9.5 being a more preferred pH.

In addition to the method set forth above, the present invention includes a solution or composition for practice of the method, as well as a test kit including such solution or composition.

A solution for the detection of a ligand and antiligand complex labelled with alkaline phosphatase or a tracer having alkaline phosphatase conjugated thereto in a sample to be tested comprises a mixture of bromo-chloro-indolyl phosphate (BCIP), phenazine methosulfate (PMS), and dimethylthiazol diphenyl tetrazolium (MTT) which when added to said test sample is capable of producing a colored formazan or a color change indicative of the presence of the labelled complex. Such a solution preferably contains equal amounts of phenazine methosulfate (PMS) and dimethylthiazol diphenyl tetrazolium (MTT) in combination with an excess amount of bromo-chloro-indolyl phosphate (BCIP). The ratio of bromo-chloro-indolyl phosphate (BCIP), phenazine methosulfate (PMS), and dimethylthiazol diphenyl tetrazolium (MTT) respectively in either solution or composition is preferably about 6:1:1 by weight. A preferred example of the solution would include from about 35 to 50 microliters (hereinafter "ul") of bromo-chloro-indolyl phosphate (BCIP) from a 50 mg/ml aqueous solution, from about 70 to 100 ul of phenazine methosulfate (PMS) from a 10 mM aqueous solution, and from about 70 to 100 ul of dimethylthiazol diphenyl tetrazolium (MTT) from a 10 mM aqueous solution. This preferred solution allows for a more controlled production of colored formazan or color change which is particularly beneficial when working with multiple test samples using alkaline phosphatase as a label. However, a solution which would include from about 35 to 50 microliters of bromo-chloro-indolyl phosphate (BCIP) from a 50 mg/ml aqueous solution, from about 100 to 700 ul of phenazine methosulfate (PMS) from a 10 mM aqueous solution, and from about 100 to 700 ul of dimethylthiazol diphenyl tetrazolium (MTT) from a 10 mM aqueous solution will be sufficient to more quickly produce a colored formazan or color change in reaction with an alkaline phosphatase labelled complex. The solution may further include a buffer such as distilled water or a buffer which is a mixture in solution of Tris-HCl or Tris-base, sodium chloride (NaCl), and magnesium chloride (MgCl$_2$). The buffered solution preferably has a pH of about 7 to about 11 with a 9.5 pH being more preferred. The solution of the present invention when reacted with a ligand and antiligand complex labelled with alkaline phosphatase or a tracer having alkaline phosphatase conjugated thereto in a sample to be tested is capable of producing a colored formazan or a sufficient color change indicative of the presence and/or concentration of the labelled complex within fifteen minutes of contacting the test sample at ambient temperature. The intensity or degree of color change is sufficient to accurately determine visually or instrumentally the presence and/or concentration of the labelled complex in the test sample.

The present invention also includes a composition for the detection of a ligand and antiligand complex labelled with alkaline phosphatase or a tracer having alkaline phosphatase conjugated thereto in a sample to be tested comprising a powder or compressed solid or a tablet mixture of bromo-chloro-indolyl phosphate (BCIP), phenazine methosulfate (PMS), and dimethylthiazol diphenyl tetrazolium (MTT) which, when dissolved in solution and added to said test sample, is capable of producing a colored formazan or a color change indicative of the presence of the labelled complex. Bromo-chloro-indolyl phosphate (BCIP), phenazine methosulfate (PMS), and dimethylthiazol diphenyl tetrazolium (MTT) naturally exist in a powdered form and may be packaged together in a powder mixture. Alternatively, these powdered ingredients may be compressed into solid form or tableted with an inert carrier, preferably an inert carrier which is soluble in water, such as mannitol, by compression or other techniques for tableting known in the tableting arts. The powder or compressed solid or tablet mixture of the composition of the present invention preferably contains approximately equal amounts of phenazine methosulfate (PMS) and dimethylthiazol diphenyl tetrazolium (MTT) in combination with an excess of bromo-chloro-indolyl phosphate (BCIP). The ratio of bromo-chloro-indolyl phosphate (BCIP), phenazine methosulfate (PMS), and dimethylthiazol diphenyl tetrazolium (MTT) respectively in such preferred composition is about 6:1:1 by weight.

The present invention may also include a kit of materials for performing the method of detection of a ligand and antiligand complex labelled with alkaline phosphatase or a tracer having alkaline phosphatase conjugated thereto disclosed herein that comprises a solution vial of, or a composition packet of, bromo-chloro-indolyl phosphate (BCIP), phenazine methosulfate (PMS), and dimethylthiazol diphenyl tetrazolium (MTT) in an amount sufficient, when reacted with said labelled complex, to produce a colored formazan or a color change indicative of the presence of the labelled complex.

The following examples are provided to further describe the invention but are in no way to be considered as limitative of the invention.

EXAMPLE I

A comparison was made between a prior art nonradioactive DNA labelling and detection method based on a BCIP and NBT chromogenic determination to the method of the present invention in two separate test protocols.

With the exception of the chromogenic determination step, each method used a Southwestern blot procedure in general accordance with the protocol of Boehringer Mannheim Corporation (Indianapolis, Ind.) Nonradioactive DNA Labeling and Detection Kit (Catalogue number 1093 657). DNA was labelled for both the prior art method and the method of the present invention by random primed incorporation of digoxigenin-labelled deoxyuridine-triphosphate. The dUTP was linked via a spacer-arm to the steroid hapten digoxigenin (Dig-dUTP). The labelling reaction was fast (1 hour) and resulted in Digoxigenin incorporation every 20–25 nucleotide in the newly synthesized DNA. This density of haptens in the DNA resulted in a high sensitivity in the prior art detection reaction, and an even significantly higher degree of sensitivity in the detection reaction of the present invention. After hybridization to the target DNA, the hybrids were detected by enzyme-linked immunoassay using an antibody-conjugate (anti-digoxigenin alkaline phosphatase conjugate, <Dig->AP) and a subsequent enzyme-catalyzed color reaction. Specifically, two prior art color reactions were initiated at alkaline pH with an equivalent of 0.00175 grams of 5-bromo-4-chloro-3-indolyl phosphate (BCIP) and an equivalent of 0.003 grams of nitroblue tetrazolium salt (NBT), each of which resulted in the formation of a blue precipitate which was only slightly observable by the naked eye in approximately four hours. Each of the two prior art color reactions of BCIP and NBT could have continued for up to three days, but each reaction was terminated after four hours. Each of the BCIP and NBT prior art reactions were performed in comparison to two color reactions performed in accordance with the teachings of the present invention. The first of the present invention chromogenic determinations used an equivalent of 0.00175 grams BCIP, 0.00214438 grams phenazine methosulfate (PMS), and 0.00290031 grams dimethylthiazol diphenyl tetrazolium (MTT). This reaction of BCIP, PMS, and MTT with the alkaline phosphatase labelled DNA resulted in the formation of a deep purple formazan within one minute and the reaction was stopped in one and a half minutes as background color started to appear. The second chromogenic determination in accordance with the present invention used the same amount of BCIP, namely an equivalent of 0.00175 grams, but reduced the amount of PMS and MTT by a factor of ten, namely an equivalent of 0.000214438 grams PMS and an equivalent of 0.000290031 grams MTT. This second reaction of BCIP, PMS, and MTT with the alkaline phosphatase labelled DNA resulted in the formation of a deep purple formazan within fifteen minutes and the reaction was stopped in twenty minutes as background color started to appear.

For all assays, DNA labelling and experimental procedure was performed substantially in accordance with the following standard Southwestern blot technique and appropriate vials of Boehringer Mannheim Corporation (Indianapolis, Ind.) Nonradioactive DNA Labeling and Detection Kit (Catalogue number 1093 657):

I. DNA labelling: 1 ug (microgram) of linear DNA was labelled per standard reaction via the control and experimental procedure below.

1. The linearized DNA was purified by phenol/-chloroform extraction and ethanol precipitation.
2. The DNA was denaturated by heating for 10 min at 95° C. and chilling quickly on ice.
3. The following was added to a microfuge tube on ice:
   1 ug of freshly denatured DNA, corresponding to 5 control-DNA (vial 2);
   2 ul hexanucleotide mixture (vial 5);
   2 ul dNPT labeling mixture (vial 6);
   1 ul Klenow enzyme (vial 7); and
   19 ul deionized water.
4. The tube was incubated for one hour at 37° C. Longer incubation (up to 20 h) can increase the amount of labelled DNA.
5. The reaction was stopped by adding 2 ul EDTA solution, 0.2 mol/l, pH 8.0, to the tube.
6. The labelled DNA was precipitated with 2 ul LiCl, 4 mol/l, and 60 ul prechilled (−20° C.) ethanol, mixed well.
7. The tube was left for 2 hours at −20° C.
8. The tube was centrifuged (at 12000 g); the pellet was washed with cold ethanol 70% (v/v), and dried under vacuum and dissolve in 50 ul Tris-HCl. 10 mmol/l; EDTA, 1 mmol/l; pH 8.0.

II. Experimental Procedure

1. Nitrocellulose membrane filters were prepared by presoaking in IPTG and then air dried on Whatman filter paper.
2. The plaques to be probed were transferred to a nitrocellulose membrane by standard Southwestern transfer plaque lift.
3. The DNA probe was labelled according to the standard assay procedure (section I).
4. The filters were then used directly for detection of hybridized DNA rather than stored air-dried for later detection.

The above labelling and plaque transfer steps are known in the art. Immunological detection of the labelled and hybridized sample preparations were made in accordance with the following protocol.

III. Immunological Detection

Four buffer solutions were prepared and used for the prior art BCIP-NBT method of detection and the present invention BCIP-PMS-MTT method of detection:

(1) Buffer 1: Tris-HCl, 100 mmol/l; NaCl., 150 mmol/l; pH 7.5 (20° C.);
(2) Buffer 2: Blocking reagent, standard 5% non-fat dried milk (blotto buffer);
(3) Buffer 3: Tris-HCl, 100 mmol/l; NaCl, 100 mmol/l; $MgCl_2$, 50 mmol/l; pH 9.5 (20° C.); and
(4) Buffer 4: Tris-HCl, 10 mmol/l; EDTA, 1 mmol/l; pH 8 (20° C.).

Each of the two solutions (freshly prepared) of BCIP-NBT consisted of 45 ul NBT-solution (vial 9) and 35 ul 5-bromo-4-chloro-3-indolyl phosphate solution added to 10 ml buffer 3 above.

The first test of the BCIP-PMS-MTT chromogenic detection in accordance with the present invention used a solution (freshly prepared) of 35 ul BCIP (50 mg/ml), 700 ul PMS (10 mM), and 700 ul MTT (10 mM) added to 10 ml buffer 3 above.

The second test of the BCIP-PMS-MTT chromogenic detection of the present invention used a solution (freshly prepared) of 35 ul BCIP (50 mg/ml), 70 ul PMS (10 mM), and 70 ul MTT (10 mM) added to 10 ml buffer 3 above.

The following control and experimental procedures were used in all of the comparative samples, the only difference being the type of and amount of chromogenic agent added to provoke the detection.

Control and experimental procedure
1. The nitrocellulose filters were washed briefly (1 min) in buffer 1. The filters were then blocked with buffer 2.
2. The antibody-conjugate was diluted to 150 mU/ml (1:5000) in buffer 1. (Dilute antibody-conjugate solutions are stable only for about 12 hours at +4° C.).
3. The filters were incubated for 30 min with about 40 ml of diluted antibody-conjugate solution. 4. Unbound antibody-conjugate was removed by washing 2×15 rain with 100 ml of buffer 1.
5. Equilibration of membranes was performed for 2 min with 20 ml of buffer 3.
6. The nitrocellulose filters were incubated with ca. 10 ml color solution.
7. When the desired spots were detected, the reaction was stopped by washing the membrane for 2 minutes with 15–20 ml of buffer 4.
8. The filters were placed on Whatman filter paper and allowed to dry at room temperature.

The following results were obtained relative to the detection:

IV. Results

Each of the two standard BCIP-NBT detection method tests resulted in the formation of a purple formazan visible to the naked eye in approximately four hours and the reaction was then stopped although the reaction could have been allowed to continue to completion in 24 hours up to three days. The first detection test using the solution containing the greater amounts of PMS and MTT with the same amount of BCIP resulted in a deep purple formazan within one minute and the reaction was then stopped in one and a half minutes as background color started to appear. Specifically, this first detection protocol used an equivalent of 0.00175 grams BCIP (an excess amount), 0.00214438 grams PMS, and 0.00290031 grams MTT. The second detection test of the present invention, which used a solution with one tenth of the amount of PMS and MTT previously used (with the same amount of BCIP), resulted in a purple formazan visible by the naked eye in fifteen minutes and the reaction was stopped in twenty minutes as background color started to appear. It is noted that for this second detection test the amount of MTT and PMS used was approximately one-tenth of the amount of NBT used. Specifically, the second test protocol performed used an equivalent of 0.00175 grams BCIP (an excess amount), 0.000214438 grams PMS, and 0.000290031 grams MTT whereas the prior art detection protocol used an equivalent of 0.00175 grams BCIP (an excess amount), and 0.003 grams NBT.

EXAMPLE II

In addition to the usage of the present invention with a nucleic acid/protein/antibody system of Example I above, a test was made of the reaction of four varying test samples having alkaline phosphatase. Table I generally describes the experiment:

TABLE I

| Test Tube No. | Contents | Reaction rests |
|---|---|---|
| 1 | AP + BCIP + NBT | No detection color change within 1 hr. |
| 2 | AP + BCIP + MTT + PMS | Instantaneous detection color change |
| 3 | AP + MTT + PMS | No detection color change within 1 hr. |
| 4 | AP + BCIP + MTT | No detection color change within 1 hr. |

In the experiment 5 ul of alkaline phosphatase from a concentrated aqueous stock solution was added to each of four test tubes. The alkaline phosphatase was colorless in solution. Next, from a 50 mg/ml aqueous stock solution of BCIP, 5 ul of BCIP (an excess amount) was added to each of test tubes numbers 1, 2, and 4 containing alkaline phosphatase. The BCIP was colorless in solution and when mixed with the alkaline phosphatase, the mixture remained colorless. Next, 10 ul of NBT solution, a lemon yellow solution, was added to Test Tube No. 1 which changed the previously colorless solution of BCIP and alkaline phosphatase to a lemon yellow color indicating the presence of NBT but not alkaline phosphatase as there was no deep color change produced within one hour of NBT being placed in admixture with the BCIP and alkaline phosphatase. Next, a 10 mM aqueous stock solution of PMS (a faint tanish color solution) and a 10 mM aqueous stock solution of MTT (a yellowish color solution) was prepared. To Test Tube No. 2 containing 5 ul of alkaline phosphatase and 5 ul of BCIP, there was added 5 ul of the stock solution of PMS and 5 ul of the stock solution of MTT which resulted in an instantaneous color change of the solution to a purplish/black deep colored solution, the solution later having settled formazan, indicative of the presence of alkaline phosphatase. Next, 5 ul of stock solution of PMS and 5 ul of the stock solution of MTT was added to Test Tube No. 3 containing 5 ul of alkaline phosphatase (no BCIP present). This addition changed the previously colorless alkaline phosphatase solution to a lemon yellow color indicating the presence of MTT but not alkaline phosphatase as there was no deep color change produced within one hour. Finally, 5 ul of MTT was added to Test Tube No. 4 containing 5 ul of alkaline phosphatase solution and 5 ul of BCIP solution. This addition changed the previously colorless alkaline phosphatase and BCIP solution to a lemon yellow color indicating the presence of MTT but not alkaline phosphatase as there was no deep color change produced within one hour.

EXAMPLE III

Another experiment was performed similar to Example II but using a Whatman filter paper instead of test tubes. Table II below generally describes the experiment:

TABLE II

| Whatman Filter Paper Spot No. | Contents Added | Reaction rests |
|---|---|---|
| 1 | AP + BCIP + NBT | No formazan within 1 hour |
| 2 | AP + BCIP + MTT + PMS | Dark purple formazan complex within 1 minute |
| 3 | AP + MTT + PMS | No formazan within 1 hour |
| 4 | AP + BCIP + MTT | No formazan within 1 hour |

This experiment utilized the aqueous stock solutions of alkaline phosphatase, PMS, and MTT described in Example II above. Four spots of 5 ul of alkaline phosphatase solution was added to separate locations of one sheet of Whatman filter. Next, from the 50 mg/ml aqueous stock solution of BCIP referred to in Example II above, 5 ul of BCIP (an excess amount) was added to alkaline phosphatase spots numbers 1, 2, and 4. Then 10 ul of NBT was added to spot number 1. The addition of NBT left a yellowish stain but did not result in the formation of a color formazan within one hour. Next, 5 ul of stock solution of MTT and 5 ul of PMS was added to spot 2 (alkaline phosphatase and BCIP). This resulted in the formation of a dark purple formazan complex at the spot in less than one minute. To spot number 3 (having no BCIP) was added 5 ul of MTT, which resulted in a yellowish stain on the spot. Then 5 ul of PMS was added to spot number 3 which stained the spot with a faint brownish color stain in combination with the MTT but resulted in no colored formazan being produced within one hour. Next to spot number 4 was added 5 ul of BCIP and 5 ul of MTT which left a yellowish stain to the previously white paper but did not result in the formation of a colored formazan after one hour.

EXAMPLE IV

This is a prophetic example relating to the identification of proteins synthesized by recombinant gene. First, a cloned bacteria, such as E-coli is grown and transferred to nitrocellulose paper or, alternatively, an extraction of proteins from a cloned bacteria is performed by SDS-gel. Next, the E-coli is lysed with chloroform or, alternatively, a western blotting of proteins on the nitrocellulose paper is performed which results in protein being affixed to the nitrocellulose paper from lysed bacteria or SDS-gel respectively. For example, the protein can be a protein of metabolized drug of abuse or a protein of a viral disease. Next, a first antibody, for example an antibody specific for glycoprotein 120 or the antibody against Lyme disease, is bound to the protein to be detected from the cloned bacteria to form a first antibody-protein complex. Next, a second antibody, such as a blotting grade conjugate of goat anti-mouse IgG, goat anti-rabbit IgG, or goat anti-human IgG, conjugated with alkaline phosphatase is bound to the first antibody-protein complex to form a first and second antibody and alkaline phosphatase complex.

Next, a positive detection of the protein is made by the addition of a solution of BCIP and MTT and PMS to the complex sufficient to generate a chromogenic deep color change or a purple/blue formazan indicative of the presence and concentration of the protein.

The experiments set forth in EXAMPLES I, II, and III, above demonstrate the surprisingly superior ability of a mixture of BCIP, PMS, and MTT, in combination, to detect alkaline phosphatase. Examples II and III are specifically intended as being universal demonstrations of the applicability of a mixture of BCIP, PMS, and MTT, in combination, to chromogenically detect alkaline phosphatase when alkaline phosphatase is used in any system for detection purpose. One skilled in the art will therefore appreciate that the method of chromogenic detection of the present invention (and solution and composition therefor) may be used in any system utilizing alkaline phosphatase as a label including, for example, such a system addressed to inorganic analyte detection. It will be understood that the specification and examples are illustrative but not limitative of the present invention and that other embodiments within the spirit and scope of the invention will suggest themselves to those skilled in the art. Many modifications and variations of the invention as heretofore set forth can be made without departing from the scope thereof and therefore only such limitations should be imposed as are indicated by the appended claims.

I claim:

1. A non-radioactive method of detecting a ligand and antiligand complex labelled with alkaline phosphatase or a tracer having alkaline phosphatase conjugated thereto comprising reacting said complex with bromo-chloro-indolyl phosphate, phenazine methosulfate and dimethylthiazol diphenyl tetrazolium and allowing the reaction to proceed to produce a colored formazan or a color change indicative of the presence of said labelled complex.

2. The method of claim 1 wherein said ligand is selected from the group consisting of an antigen, an analyte, a protein, an antibody, an antibody complex, and a hapten.

3. The method of claim 1 wherein said antiligand is selected from the group consisting of an antigen, an analyte, a protein, an antibody, an antibody complex, and a hapten.

4. The method of claim 2 wherein said ligand is an antigen and said antiligand is an antibody specific for said antigen.

5. The method of claim 2 wherein said ligand is a hapten and said antiligand is an antibody specific for said hapten.

6. The method of claim 2 wherein said ligand is an antibody and said antiligand is an antigen specific for said antibody.

7. The method of claim 2 wherein said ligand is a protein and said antiligand is an antibody specific for said protein.

8. The method of claim 2 wherein said ligand is a nucleic acid and said antiligand is a complimentary nucleic acid specific for said nucleic acid.

9. The method of claim 2 wherein said ligand is an antibody complex and said antiligand is an antigen specific for said antibody complex.

10. The method of claim 1 wherein a ligand directly labelled with alkaline phosphatase and a tracer selected from the group consisting of an antigen, an analyte, a protein, an antibody, an antibody complex, and a hapten compete for binding sites on said antiligand.

11. The method of claim 1 wherein a ligand selected from the group consisting of an antigen, an analyte, a protein, an antibody, an antibody complex, and a hapten and a tracer having alkaline phosphatase conjugated thereto compete for binding sites on said antiligand.

12. The method of claim 1 wherein the amount, intensity, or degree of produced colored formazan or color change is determined visually or instrumentally.

13. The method of claim 1 wherein the complex is reacted with a mixture containing in combination bromo-chloro-indolyl phosphate, phenazine methosulfate and dimethylthiazol diphenyl tetrazolium.

14. The method of claim 13 wherein said mixture further includes a buffer.

15. The method of claim 14 wherein said buffer is distilled water.

16. The method of claim 14 wherein said buffer is a mixture in solution of Tris-HCl or Tris-base, sodium chloride, and magnesium chloride.

17. The method of claim 14 wherein the buffer has a pH of 7 to 11.

18. The method of claim 14 wherein the buffer has a pH of 9.5.

19. A solution for the detection of a ligand and antiligand complex labelled with alkaline phosphatase or a tracer having alkaline phosphatase conjugated thereto in a sample to be tested comprising a mixture of bromo-chloro-indolyl phosphate, phenazine methosulfate and dimethylthiazol diphenyl tetrazolium which when added to said test sample is capable of producing a colored formazan or a color change indicative of the presence of said labelled complex.

20. The solution of claim 19 containing approximately equal amounts of phenazine methosulfate and dimethylthiazol diphenyl tetrazolium in combination with an excess of bromo-chloro-indolyl phosphate.

21. The solution of claim 19 wherein the ratio of bromo-chloro-indolyl phosphate, phenazine methosulfate and dimethylthiazol diphenyl tetrazolium respectively in said solution is about 6:1:1 by weight.

22. The solution of claim 19 including from 35 to 50 microliters of bromo-chloro-indolyl phosphate from a 50 mg/ml aqueous solution, from 70 to 100 microliters of phenazine methosulfate from a 10 mM aqueous solution and from 70 to 100 microliters of dimethylthiazol diphenyl tetrazolium from a 10 mM aqueous solution.

23. The solution of claim 19 capable of producing a sufficient colored formazan or a color change indicative of the presence or concentration of said complex within fifteen minutes of contacting at ambient temperature said test sample.

24. The solution of claim 19 wherein the amount, intensity, or degree of the produced colored formazan or color change is sufficient to accurately determine visually or instrumentally the presence or concentration of said complex in said test sample.

25. The solution of claim 19 further including a buffer.

26. The solution of claim 25 wherein the buffer is distilled water.

27. The solution of claim 25 wherein the buffer is a mixture in solution of Tris-HCl or Tris-base, sodium chloride, and magnesium chloride.

28. The solution of claim 25 wherein the buffer has a pH of 7 to 11.

29. The solution of claim 25 wherein the buffer has a pH of 9.5.

30. A composition for the detection of a ligand and antiligand complex labelled with alkaline phosphatase or a tracer having alkaline phosphatase conjugated thereto in a sample to be tested comprising a mixture of bromo-chloro-indolyl phosphate, phenazine methosulfate and dimethylthiazol diphenyl tetrazolium which when dissolved in solution and added to said test sample is capable of producing a colored formazan or a color change indicative of the presence of said labelled complex.

31. The composition of claim 30 in powder form.

32. The composition of claim 30 in solid form.

33. The composition of claim 30 further including an inert carrier.

34. The composition of claim 30 wherein the inert carrier is soluble in water.

35. The composition of claim 30 wherein the inert carrier is mannitol.

36. The composition of claim 30 containing approximately equal amounts of phenazine methosulfate and dimethylthiazol diphenyl tetrazolium in combination with an excess of bromo-chloro-indolyl phosphate.

37. The composition of claim 30 wherein the ratio of bromo-chloro-indolyl phosphate, phenazine methosulfate and dimethylthiazol diphenyl tetrazolium respectively in said composition is about 6:1:1 by weight.

38. A kit of materials for performing the method of detection of a ligand and antiligand complex labelled with alkaline phosphatase or a tracer having alkaline phosphatase conjugated thereto according to claim 1, comprising a vial or packet of bromo-chloro-indolyl phosphate, phenazine methosulfate and dimethylthiazol diphenyl tetrazolium in an amount sufficient, when reacted with said labelled complex, to produce a colored formazan or a color change indicative of the presence of said labelled complex.

* * * * *